US005549601A

United States Patent [19]
McIntyre et al.

[11] Patent Number: 5,549,601
[45] Date of Patent: Aug. 27, 1996

[54] DELIVERY OF INTRACORPOREAL PROBES

[75] Inventors: John McIntyre, San Carlos; Peter S. Brown, Mountain View; Stephen A. Morse, Palo Alto, all of Calif.

[73] Assignee: Devices for Vascular Intervention, Inc., Redwood City, Calif.

[21] Appl. No.: 321,398

[22] Filed: Oct. 11, 1994

[51] Int. Cl.⁶ ........................................... A61B 17/36
[52] U.S. Cl. .............................. 606/15; 606/14; 606/10; 600/108
[58] Field of Search ................................ 606/3, 7, 13–17; 604/95; 600/108; 607/89

[56] References Cited

U.S. PATENT DOCUMENTS

| | | |
|---|---|---|
| 3,352,303 | 11/1967 | Delaney . |
| 3,433,226 | 3/1969 | Boyd . |
| 4,223,676 | 9/1980 | Wuchinich et al. . |
| 4,445,509 | 5/1984 | Auth . |
| 4,646,736 | 3/1987 | Auth . |
| 4,732,154 | 3/1988 | Shiber . |
| 4,749,376 | 6/1988 | Kensey et al. . |
| 4,798,586 | 1/1989 | Stevens . |
| 4,854,325 | 8/1989 | Stevens . |
| 4,923,462 | 5/1990 | Stevens . |
| 4,990,134 | 2/1991 | Auth . |
| 5,090,956 | 2/1992 | McCoy .................................. 604/95 |
| 5,151,096 | 9/1992 | Khoury ................................ 606/7 X |
| 5,188,634 | 2/1993 | Hussein et al. ...................... 606/15 |
| 5,243,997 | 9/1993 | Uflacker et al. . |
| 5,267,954 | 12/1993 | Nita . |
| 5,290,279 | 3/1994 | Bonati et al. ....................... 606/7 X |
| 5,304,115 | 4/1994 | Pflueger et al. . |
| 5,312,328 | 5/1994 | Nita et al. . |
| 5,312,392 | 5/1994 | Hofstetter et al. ................. 606/16 X |
| 5,324,255 | 6/1994 | Passafaro et al. . |
| 5,326,342 | 7/1994 | Pflueger et al. . |
| 5,330,465 | 7/1994 | Doiron et al. ........................ 606/7 |
| 5,344,395 | 9/1994 | Whalen et al. . |
| 5,345,940 | 9/1994 | Seward et al. . |
| 5,383,859 | 1/1995 | Sewell, Jr. ........................ 606/180 X |

FOREIGN PATENT DOCUMENTS

| | | |
|---|---|---|
| 0268228A2 | 5/1988 | European Pat. Off. . |
| 452631 | 10/1991 | European Pat. Off. ............... 606/191 |
| 0465449A2 | 1/1992 | European Pat. Off. . |

OTHER PUBLICATIONS

Louis Lapicque, "Experimental Definition of Excitability", Proc. Soc. de Biol., vol. 77, pp. 280–285, 1909.
Brochure by Indigo® Medical Incorporated, "Indigo Diffuser-Tip™ Fiberoptics", Copyright Indigo Medical, Inc. 1994, 86–655 Rev. A01 (5M).

Primary Examiner—Angela D. Sykes
Assistant Examiner—Michael Peffley
Attorney, Agent, or Firm—Crosby, Heafey, Roach & May

[57] ABSTRACT

A system for delivering a probe into a body part to perform a therapeutic or diagnostic procedure therein which includes an elongated probe device which is disposed within a protective sheath and which has a rotary drive unit connected to its proximal extremity to rotate the probe about its longitudinal axis, preferably at a rate above 50 rpms while applying axial pressure thereto to cause the distal end of the probe to penetrate through the patient's tissue to a desired location in the body part where the procedure is to occur. In a presently preferred embodiment, the probe is an optical fiber which is delivered into a male patient's prostate gland through the patient's prostatic urethral wall. The optical fiber is optically connected to a source for laser energy (815 nm) which is emitted from the distal end of the optical fiber to ablate prostatic tissue surrounding the distal end. A sheath is disposed about the optical fiber to support the shaft thereof and to minimize damage to the working channel of a cystoscope through which the device is usually advanced to reach the desired location within the patient's prostatic urethra.

15 Claims, 2 Drawing Sheets

DELIVERY OF INTRACORPOREAL PROBES

BACKGROUND OF THE INVENTION

This invention relates to the intracorporeal delivery of elongated therapeutic and diagnostic probe devices and particularly to such devices for the treatment of benign prostatic hyperplasia (BPH).

BPH is the enlargement of the prostate gland which frequently occurs in men as they grow older. The enlarged gland can constrict the urethral canal, interfering with the flow of urine through the canal. Treatment modalities for the BPH condition has varied over the years. For many years constricted urethral passageways were dilated by passing bogies with increasing larger distal tips through the constricted passageway. More recently, a similar method has been employed whereby a catheter having a dilatation balloon on its distal end is advanced through the patient's urethra until the dilatation balloon is disposed within the stenotic region and then the balloon is inflated to dilate the urethral passageway. The expansion of the urethral canal through the stenotic region can be effective in expanding the passageway, but the benefits are frequently short-lived, in that the constriction returns after a year or two after the initial dilatation.

The most frequently used modality is the transurethral resection of the prostate (TURP) which involves insertion of a resectoscope through the urethra and removing the constricting tissue by means of a hot wire. However, such surgery can result in incontinence, impotence and a variety of other problems. It usually requires general anaesthesia and a significant hospital stay.

Another treatment modality of more recent origin involves debulking the prostate gland by laser energy which is delivered into the gland by means of an optical fiber. For example, PCT application WO 92/10142 (Makower) describes the utilization of a catheter which is advanced into the patient's urethral canal until its distal end is situated within the prostatic urethra and an elongated needle is curved out of the distal end of the catheter into an adjacent lobe of the patient's prostate gland. An optical fiber is advanced through the inner lumen of the needle into the prostate gland and laser energy is emitted from the distal end of the optical fiber to ablate prostatic tissue. A preferred embodiment has facilities to advance a pair of elongated needles, one needle into each lobe of the prostate gland.

A laser based BPH treatment device of different design is commercially available from the Indigo Medical, Inc.

While laser based devices for BPH treatment procedures have shown promise, they have not been found to be suitable for out-patient use because these procedures use rigid cystoscopes usually requiring general anesthesia and frequently involve extended hospital stays. Due to the extended hospital stays, the treatment costs for laser based BPH treatments are not much less than the costs for TURP.

The laser devices have not been used with flexible cystoscopes because the working channels of the latter is not large enough. Moreover the shaft of the flexible cystoscope does not provide firm enough support for the optical fiber of the laser device to facilitate passage through the urethral wall and into the patient's prostate gland.

What has been needed is a laser based system which can be used with a flexible cystoscope so as to not require general anesthesia and which would facilitate BPH procedures in the physician's office. The present invention satisfies these and other needs.

SUMMARY OF THE INVENTION

This invention is directed to a method and system for penetrating into a portion of a patient's body with little axial force and with very little trauma thereto and particularly to the advancement of an optical fiber through a urethral wall into a patient's prostate gland to facilitate the debulking thereof by means of laser energy emitted from the distal end of the optical fiber.

The system of the invention basically includes a probe having proximal and distal ends with means, such as a rotary drive unit, to rotate the probe while it is urged against tissue to be penetrated. The system may also include endoscopic means such as a flexible cystoscope to guide the distal end of the probe in a desired direction toward the portion of the patient's body to be penetrated. Rotation of the probe device while it is urged against body portion to be penetrated significantly lowers the penetration force required. The rotary drive unit is powered to rotate the probe at a rate of at least 50 revolutions per minute (rpm) and as high as 20,000 rpms or more to facilitate penetration of tissue. Rotational speeds between about 200 to about 3,000 rpm are adequate for most applications. Generally, the more dense the tissue the higher the rotational speeds required for a given required penetration force. There is significant reduction in the force required for penetration at the lower rotational speeds, but at the higher rotational speeds, e.g. above 1000 rpm, there are relatively small decreases in penetration force for incremental increases in rotational speeds. By applying an axial force to the probe to press the distal end thereof against the tissue to be penetrated and rotating the probe, the distal end of the probe readily passes through the tissue with little or no trauma thereto. The advantages of the invention are obtained whether passing through tissue or between layers of tissue, the only difference is the level of axial force required.

In one presently preferred embodiment of the invention, the probe is an elongated optical fiber which has a proximal end connectable to a source of laser energy and which transmits laser energy received from the source to the distal end where it is emitted.

This preferred embodiment is particularly suitable to be used to debulk a patient's prostate gland, where the optical fiber is configured to be advanced through the working lumen of a urethral cystoscope, preferably a flexible cystoscope. The distal end of the cystoscope may be flexed or curved at an angle with respect to the longitudinal axis of the cystoscope so as to guide the distal end of the optical fiber against the urethral wall. A supporting sheath should be slidably disposed about the optical fiber to support the fiber and prevent undue wear and tear on the working lumen of the cystoscope and the optical fiber due to the rotation of the optical fiber. Alternativley, the flexible cystoscope can be modified or constructed to guide the optical fiber laterally without deflecting the distal extremity of the cyctoscope.

The device of the present invention can be used with either flexible or rigid cystoscopes, but the use with a flexible cystoscope provides greater advantages because general anesthesia may not be required. The procedure for treating BPH with the present invention in conjunction with a flexible cystoscope can be readily and safely performed on an outpatient basis in a physicians office which can significantly reduce the costs and recovery time for the procedure.

These and other advantages will become more apparent from the following detailed description of the invention when taken in conjunction with the accompanying exemplary drawings.

DETAILED DESCRIPTION OF THE INVENTION

Figure 1:
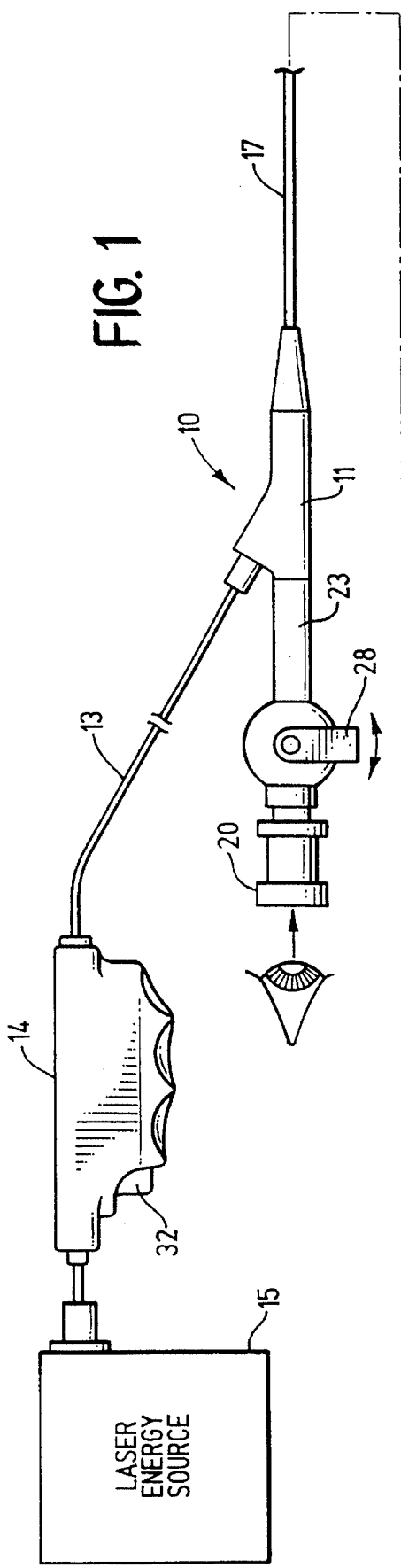
FIG. 1 is an elevational view, partially in section, of a cystoscopic assembly embodying features of the invention with the distal portion extending within a patient's prostatic urethra.

FIG. 1 illustrates a presently preferred cystoscopic assembly 10 which embodies features of the invention. The assembly 10 generally includes a cystoscope 11 (shown as a flexible cystoscope), an optical fiber 12, a protective sheath 13, a rotary drive unit 14 connected to the proximal extremity of the optical fiber and a laser source 15 optically connected to the proximal end of the optical fiber.

Figure 2:
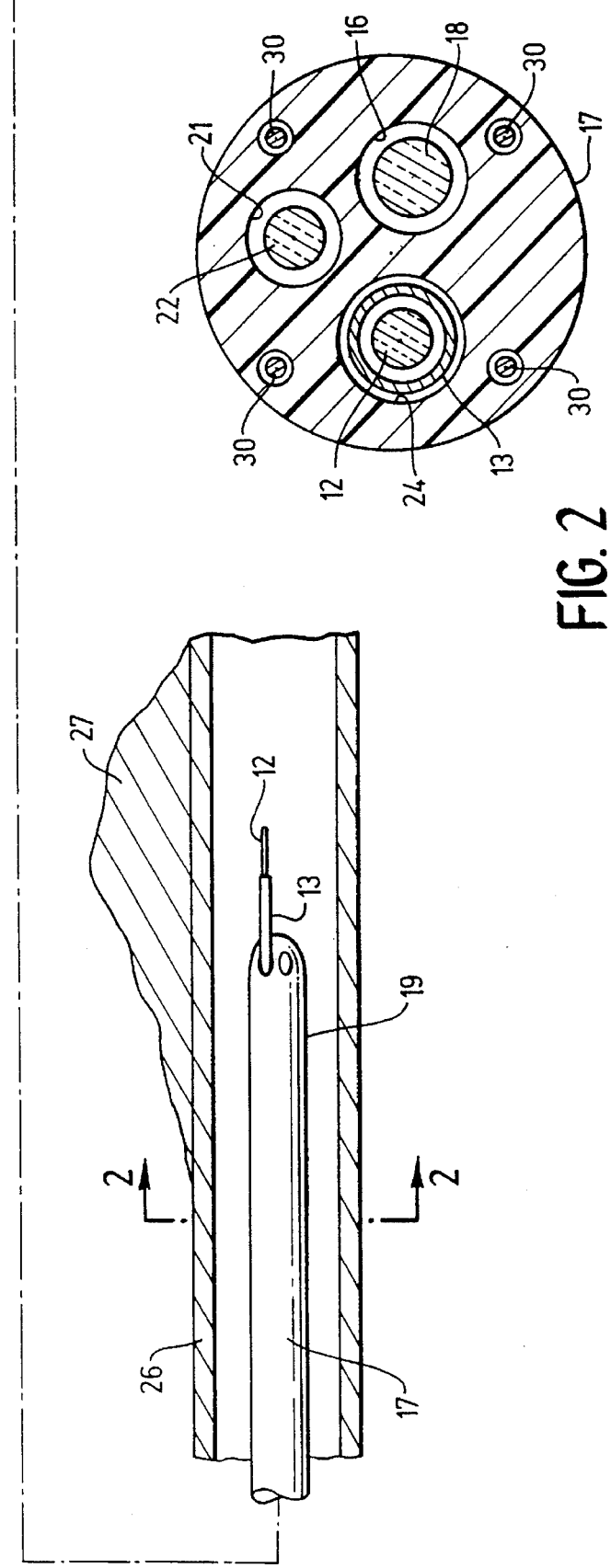
FIG. 2 is a transverse cross-sectional view of the distal tip of the assembly shown in FIG. 1 taken along the lines 2—2.
Figure 3:
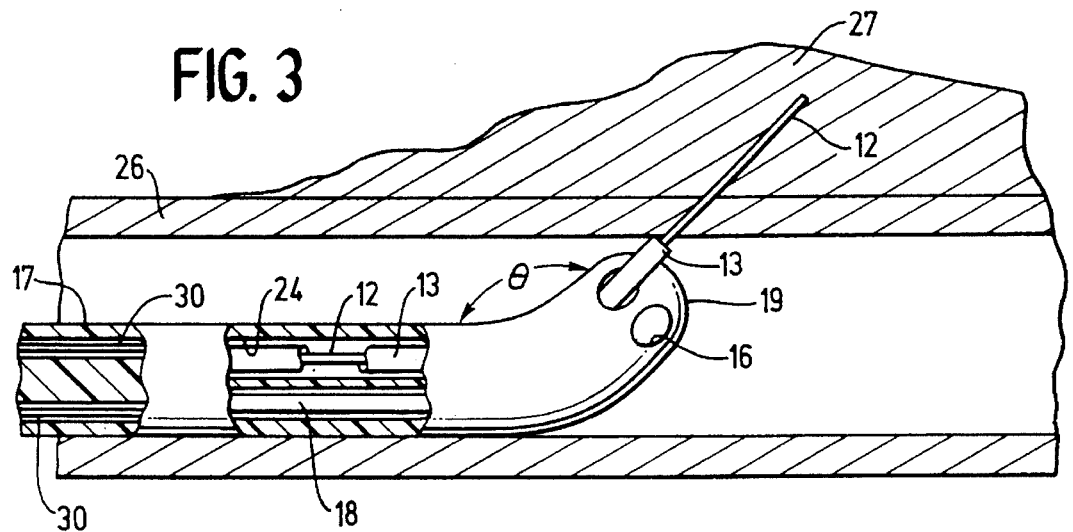
FIG. 3 is a longitudinal cross-sectional view of the distal portion of the assembly which has been deflected or curved within the patient's prostatic urethra shown in FIG. 1 and which has the optical fiber extending into the patient's prostate gland.
Figure 4:
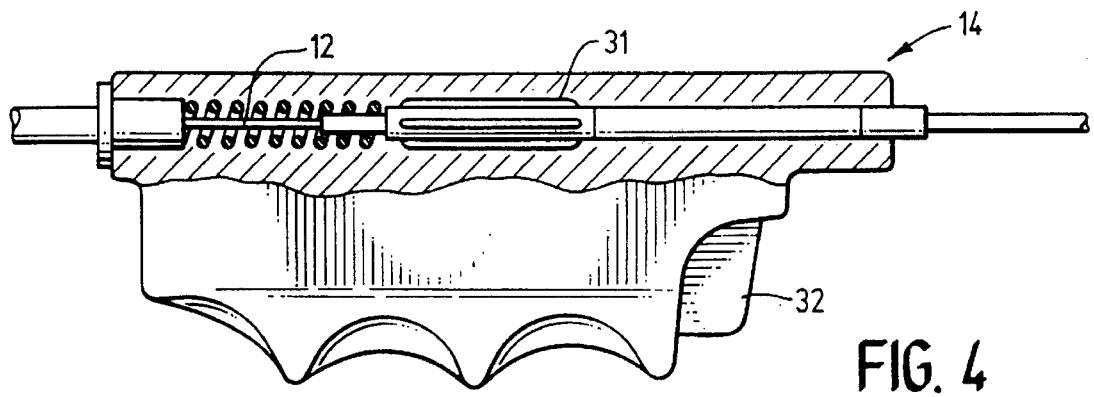
FIG. 4 is an enlarged elevational view, partially in section, of a rotary drive unit connected to the proximal extremity and the optical fiber assembly shown in FIG. 1.

The cystoscope 11, which is schematically shown in FIGS. 1 and 2, may be of conventional construction with one or more inner lumens 16 extending within the shaft 17 of the cystoscope having an optical fiber 18 therein for viewing the region about the distal end 19 of the cystoscope 11 through the eyepiece 20. A second lumen 21 extending through the cystoscope shaft 17 is provided with optical fiber 22 which is connected to a light source (not shown) in the handle 23 of the cystoscope 11 to illuminate the region around the distal end 18 of the cystoscope. A third lumen 24, a working lumen, is provided within the cystoscope shaft 17 to allow the advancement of the optical fiber 12 (or other therapeutic or diagnostic devices) through the cystoscope and out the distal end 19 thereof. The protective sheath 13, which is fixed by its proximal end to the rotary drive unit 14 and does not rotate, supports and protects the optical fiber 12 while it is advanced and rotated and prevents damaging the surface of working lumen 24 of the cystoscope 11.

As shown in FIGS. 1 and 2 the distal end 19 of the cystoscope 11 is shapable or deflectable by adjusting the lever 28 on the cystoscope handle 23. Typically, the lever 28 is connected to one or more control lines 30 which extend to the distal end 19 of the cystoscope 11 and movement of the lever applies tension to the one or more of these control lines to curve or deflect the distal end of the cystoscope in a desired direction. As shown best in FIG. 2, the cystoscope 11 is preferably provided with four control lines 30 to allow universal deflection of the distal tip 19 without the need to rotate the cystoscope.

The optical fiber 12 has a splined element 31 secured to the portion thereof which extends through the rotary drive unit 14 to facilitate operative connection to the drive means (not shown) within the drive unit. The application of pressure to trigger 32 actuates the drive unit 14 to rotate the optical fiber 12. A rotary drive unit suitable for use with the present invention are available from Devices for Vascular Intervention, Inc. the present assignee which are sold for use with a therectomy devices. The rotary drive unit 14 may be operated with a foot operated switch if desired.

Figure 5:
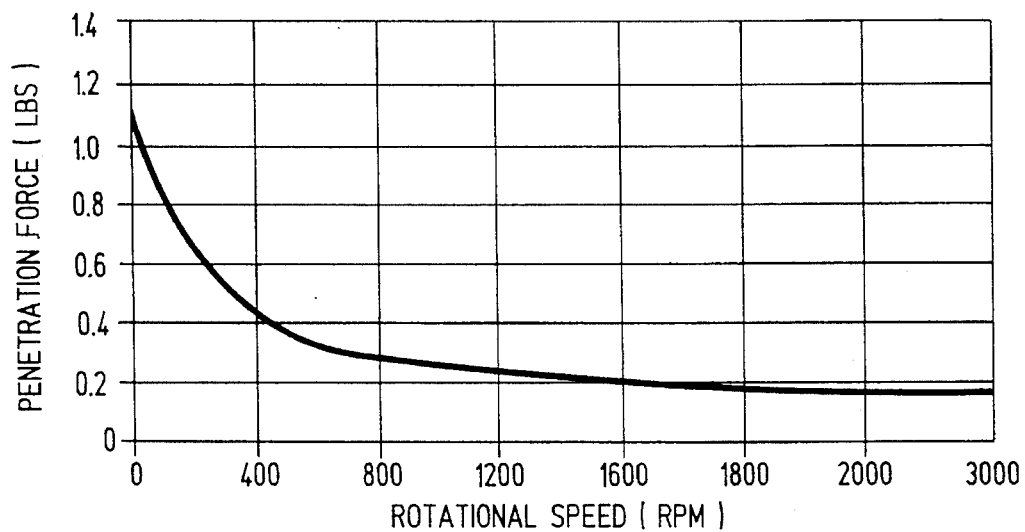
FIG. 5 is idealized graphical representation of the relationship between rotational speed of a probe and the axial force required for penetrating tissue.

To facilitate the penetration of the urethral wall 26 and the prostate gland 27 in accordance with the invention, the optical fiber 12 is rotated by the rotary drive unit 14 connected to its proximal extremity while a slight axial pressure is applied to the optical fiber from its proximal end. A rotational speed of about 200 to about 3000 rpms is suitable to readily penetrate most human tissue with an optical fiber of about 600 microns in diameter. The force required for the penetration of the distal end of the optical fiber 12 while it is rotating at these rates is substantially less than the force which would require penetration into the prostate gland 27 without the rotation. Typical reductions in penetration force needed for advancing a rotating optical fiber 12 through tissue can exceed 80% or more of the force needed for penetration of a probe without rotation. FIG. 5 graphically depicts an idealized relationship of the axial force required to advance an optical fiber through tissue at various rotational speeds up to 3000 rpms. The data shown is for a optical fiber having a diameter of about 600 microns with one or more lubricous coatings, e.g. fluoropolymer, having a total coating thickness of about 110 microns. As is evident, there is a significant decrease in the required axial force for penetration with respect to the rotational speed at speeds up to about 400 rpms and then there is a rather gradual decrease in required axial force as the rotational speed of the optical fiber is increased over about 1000 rpms. The rotary drive unit has a tendency to stall when the rotational speed is less than about 200 rpms. The penetration force required for body parts may vary depending upon the density and/or toughness of the tissue but the general relationship will still apply, i.e. the curve may be shifted up or down or to the right or left but the general shape of the curve will remain.

A laser source to 15 is connected to the proximal end of the optical fiber 12 in a light transmitting relationship and delivers laser energy at a level sufficient to be transmitted through the optical fiber and to ablate prostate tissue when emitted from the distal end of the optical fiber. For prostate and other tissue ablation, a diode laser with a wave length of about 815 nanometers is presently preferred. However, lasers at other wave lengths may be employed. The laser emission out of the distal end of the optical fiber may be focused or dispersed and may be in pulses or a continuous beam.

The laser ablation is for the most part limited to the tissue in the region surrounding or distal to the distal end of the optical fiber 12 depending upon whether the laser energy emitted from the distal end is dispersed or focused. If, after the initial ablation of the prostate tissue, other prostate tissue in the surrounding prostate region is to be ablated, the distal tip of the optical fiber 12 must be relocated within the gland. To relocate the distal tip of the optical fiber 12 to another region, the optical fiber and the sheath 13 may be withdrawn back into the cyctoscope 11 and the deflection angle of the distal end 19 of the cystoscope is changed by moving lever 28 (shown in FIG. 1) to change the angle of attack with respect to the urethral wall 26. The optical fiber 12 may then be readvanced into the prostate tissue at a slightly different angle while being rotated as previously described. Care should be exercised when adjusting the position of the optical fiber 12 because it is fragile and may break if the angle of deflection of the distal end 19 of the cystoscope is changed while the optical fiber extends out of the protective sheath 13.

After ablation of tissue in one lobe of the patient's prostate gland 27, the cystoscope 11 can be rotated and the process repeated in the opposite lobe, if needed. When both lobes of the patient's prostate gland have been adequately debulked, the cystoscope assembly can be removed from the patient's urethra. If desired, the cystoscope 11 can be provided with two working lumens 24 extending through the length of the shaft 18 with the openings thereof on opposing sides of the shaft at the distal end 19. In this embodiment, individual optical fibers 12 with sheaths 13 can be advanced through both working lumens and then into both prostatic lobes of the patient to ablate the tissue thereof. The ablation in both prostate lobes can occur simultaneously or sequentially. Means are provided in the dual working lumens for the lateral movement of the two individual optional fibers.

While the invention has been described herein primarily in terms of an assembly for treating benign prostatic hyperplasia, those skilled in the art will recognize that the invention can be employed in a wide variety of intracorporeal procedures for therapeutic or diagnostic purposes where it is desired to penetrate tissue into a desired location within a patient's body. For example, the invention may be employed when taking tissue samples for biopsy, when performing various laproscopic surgical procedures or for site specific delivering of drugs and the like to otherwise inaccessible locations within a patient's body, particularly in situations such as when treating cancer where the drugs are highly toxic and systemic delivery of the drug may not be tolerated by the patient. Those skilled in the art will recognize many other uses for the invention in addition to those mentioned above. Additionally, although individual features of embodiments of the invention may be shown in some of the drawings and not in others, those skilled in the art will recognize that individual features of one embodiment of the invention can be combined, with any or all the features of another embodiment. Various improvements can be made to the invention without departing from the scope thereof.

What is claimed is:

1. A method of performing a therapeutic or diagnostic procedure within a patient, comprising:
   a) providing an therapeutic or diagnostic assembly which includes an outer sheath having an inner lumen and a open distal end and an elongated optical fiber device having a distal end configured to emit laser energy, being slidably disposed within the inner lumen of the outer sheath and extending out the open distal end of the outer sheath;
   b) urging the distal end of the optical fiber device against tissue to be penetrated while the device is rotated within the outer sheath to place the distal end of the device at a location within the patient where the therapeutic or diagnostic procedure is to be performed; and
   c) directing laser energy through the optical fiber device and out the distal end thereof at the location in the patient.

2. The method of claim 1 wherein the optical fiber device is rotated at a speed of at least 50 rpms.

3. The method of claim 1 wherein the optical fiber device is rotated at a rotational speed of about 200 to about 3000 rpms.

4. The method of claim 1 wherein the optical fiber device has a proximal end configured to engage a laser energy source in a light transmitting relationship.

5. The method of claim 1 wherein the therapeutic or diagnostic assembly is advanced through a working channel of an endoscope disposed within a patient's body lumen.

6. The method of claim 5 wherein the endoscope has a deflectable distal end which guides the therapeutic or diagnostic assembly to the desired tissue to be penetrated.

7. A system for debulking a patient's prostate gland, comprising:
   a) a protective sheath having an inner lumen extending therein which is configured to be slidably disposed within a working lumen of a cystoscope;
   b) an elongated optical fiber having a proximal end and a distal end and being slidably disposed within the inner lumen of the protective sheath;
   c) a laser energy source in light transmitting relationship with the proximal end of the optical fiber to deliver laser energy thereto; and
   d) rotary drive means to rotate the optical fiber at a rate greater than about 50 revolutions per minute while an axial force is applied to the optical fiber to facilitate penetration by the distal end of the optical fiber through the prostatic urethra into the prostate gland.

8. The system of claim 7 including a urethral cystoscope having at least one working lumen extending therein and being configured to be advanced through a male patient's urethral canal to the patient's prostatic urethra within the patient's prostate gland with the sheath and the optical fiber disposed therein slidably disposed within the working lumen.

9. The system of claim 8 wherein the cystoscope has a flexible shaft and means operable from the proximal end thereof to deflect the distal end of the cystoscope to guide the optical fiber to a desired region of the prostatic urethra.

10. The system of claim 7 wherein the optical fiber has a diameter of about 400 to about 800 microns.

11. The system of claim 7 wherein the optical fiber has a lubricous coating on the exterior thereof.

12. A method for treating a male patient for benign prostatic hyperplasia comprising:
   a) advancing an optical fiber having proximal and distal ends through a patient's urethra until the distal end is disposed within a desired portion of the patient's prostatic urethra;
   b) pressing the distal end of the optical fiber against a wall of the patient's prostatic urethra and rotating the optical fiber until the distal end of the optical fiber passes through the wall of the prostatic urethra into a desired region of the patient's prostate gland adjacent the wall; and
   c) directing laser energy from a source thereof through the optical fiber and out the distal end thereof to ablate prostatic tissue adjacent the distal end of the optical fiber.

13. The method of claim 12 wherein the optical fiber is rotated at more than 50 rpms.

14. The method of claim 12 wherein the optical fiber is rotated at about 200 to about 3000 rpms.

15. The method of claim 12 wherein the laser energy directed out the distal end of the optical fiber has a wave length of about 815 nanometers.

* * * * *